United States Patent [19]
Wolfer

[11] Patent Number: 5,168,758
[45] Date of Patent: Dec. 8, 1992

[54] FORCE/STRAIN AND STRUCTURE-BORNE NOISE TRANSDUCER

[75] Inventor: Peter Wolfer, Kleinandelfingen, Switzerland

[73] Assignee: Kistler Instruments AG, Switzerland

[21] Appl. No.: 708,374

[22] Filed: May 31, 1991

[30] Foreign Application Priority Data

May 31, 1990 [CH] Switzerland .................. 1842/90

[51] Int. Cl.$^5$ .................................................. G01B 7/16
[52] U.S. Cl. .................................. 73/774; 73/862.044; 73/862.541
[58] Field of Search ................ 73/649, 652, 654, 653, 73/659, 660, 763, 774, 862.04, 862.05, 862.06, 862.54, 862.68, 865.9

[56] References Cited

U.S. PATENT DOCUMENTS

| | | | |
|---|---|---|---|
| 3,658,147 | 4/1972 | Ho et al. | 73/659 |
| 4,007,630 | 2/1977 | Noda | 73/659 |
| 4,869,187 | 9/1989 | Little et al. | 73/862.54 |
| 5,095,760 | 3/1992 | Lew | 73/861.24 |

*Primary Examiner*—Robert Raevis
*Attorney, Agent, or Firm*—Barnes & Thornburg

[57] ABSTRACT

A transducer combining a force or strain or both sensor in a common housing with a structure-borne noise sensor and responsive to transmissions at a common mounting surface of the housing. The transducer may be in a force transducer, a surface strain transducer, or a screw strain transducer.

16 Claims, 3 Drawing Sheets

FORCE/STRAIN AND STRUCTURE-BORNE NOISE TRANSDUCER

BACKGROUND AND SUMMARY OF THE INVENTION

For monitoring automated machine tools at important force connecting points on the machine, multicomponent force measuring sensors or strain sensors are used which divide the force flow into several coordinates. These signals are compared continuously with setpoints or predetermined values. Such machines, which operate through the so-called "witching hours", are CNC-controlled machine tools like turning and milling centers. They operate fully automatically and at the slightest deviation from the target state, a tool change or machine stop is initiated.

Such monitoring systems are already obtainable today from various machine makers as special equipment. Also available commercially are the necessary multicomponent force and strain sensors. The corresponding electronics and associated software are supplied by a number of specialized enterprises.

In recent years it has been shown that besides the machining forces, moments and strains, machine noises or structure-borne noise is another mechanical variable capable of constituting a further useful component for monitoring machining operations. Already there are boring machine monitoring devices which detect tool breakage through the alteration of the structure-borne noise spectrum. For grinding operations also, structure-borne noise measurement has proved of interest.

Measuring structure-borne noise from machining operations, as also from the drive parts, is of interest in the frequency range from 0.5 to 50 kHz. Usually, it is measured with high-frequency accelerometers. Transducers suitable for such analyses can be procured commercially today. Often, they are structure-borne noise transducers employed in automobile engineering for measuring detonation. Such transducers are big and less suited for fitting in machine tools.

The present invention combines measuring of force with structure-borne noise, and strain with structure-borne noise, to open up new application possibilities. The advantages are as follows:

Only one sensor installation point is needed.

Only one cable connection is needed.

In the domain of finish machining, structure-borne noise measuring may yield information additional to the force or strain measurement. In rough machining, the force or strain measurement, as the case may be, tells more than measuring the structure-borne noise.

In many applications, the two modes—force and strain measuring and structure-borne noise measuring—are complementary.

Other objects, advantages and novel features of the present invention will become apparent from the following detailed description of the invention when considered in conjunction with the accompanying drawings.

DETAILED DESCRIPTION OF THE DRAWINGS

Figure 1:
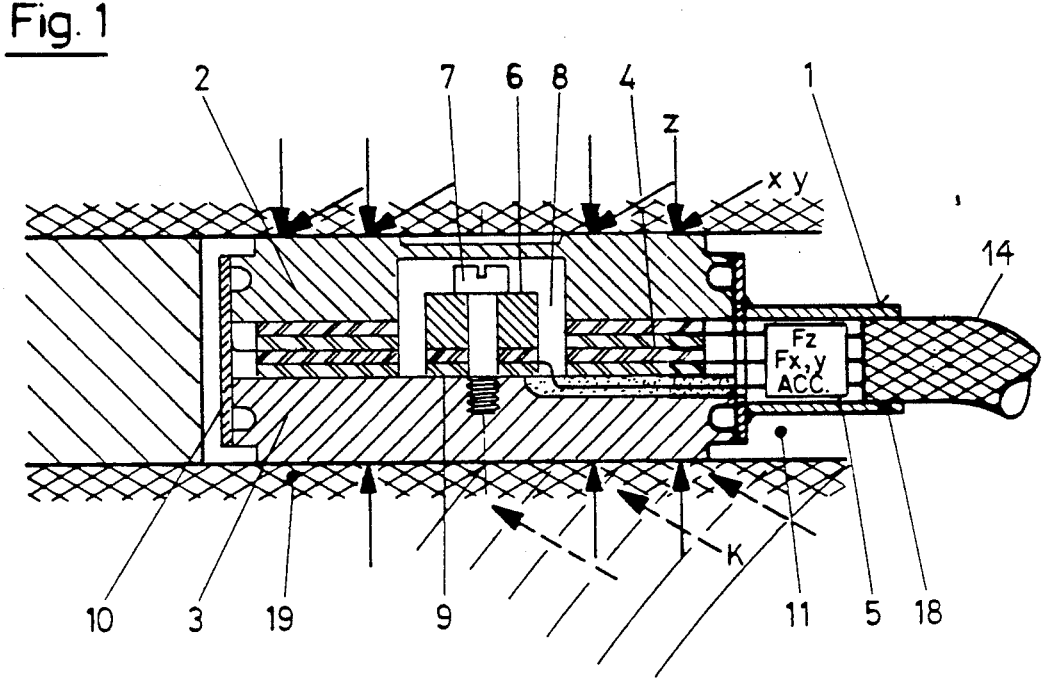
FIG. 1 is a cross-sectional view of a force and structure-borne noise transducer according to the invention for one or more force components, with structure-borne noise sensor arranged centrally.
Figure 2:
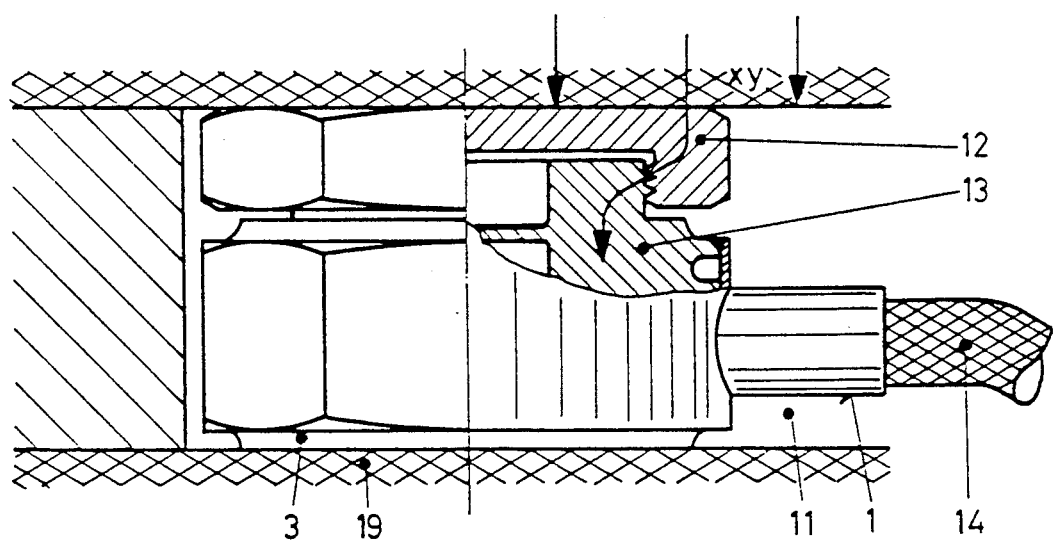
FIG. 2 shows the transducer of FIG. 1 with integrated bracing nut.
Figure 3:
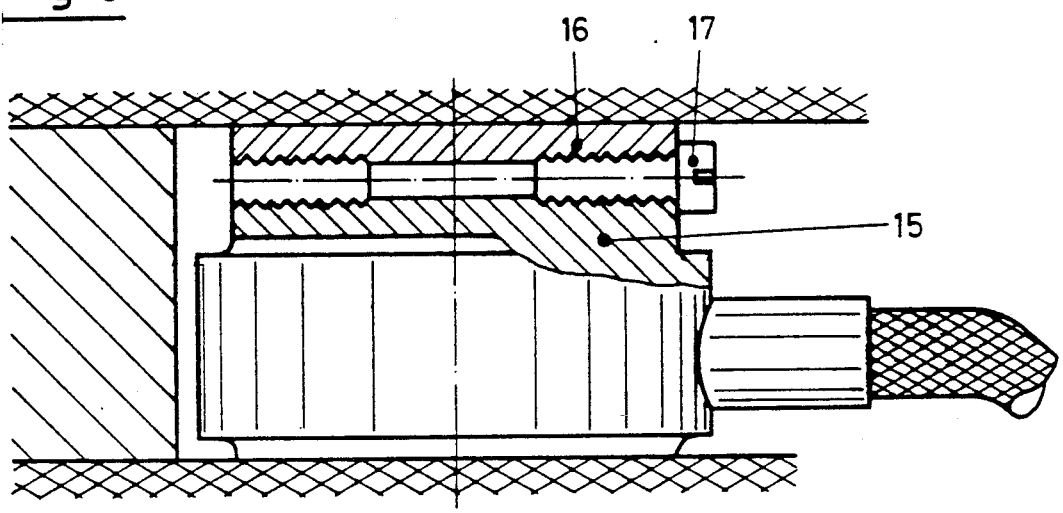
FIG. 3 shows the transducer of FIG. 1 with integrated key bracing element.

FIGS. 1-3 show single to multi-component force sensors with integrated bracing devices and built in single or multi-axis structure-borne noise sensor.

Figure 4:
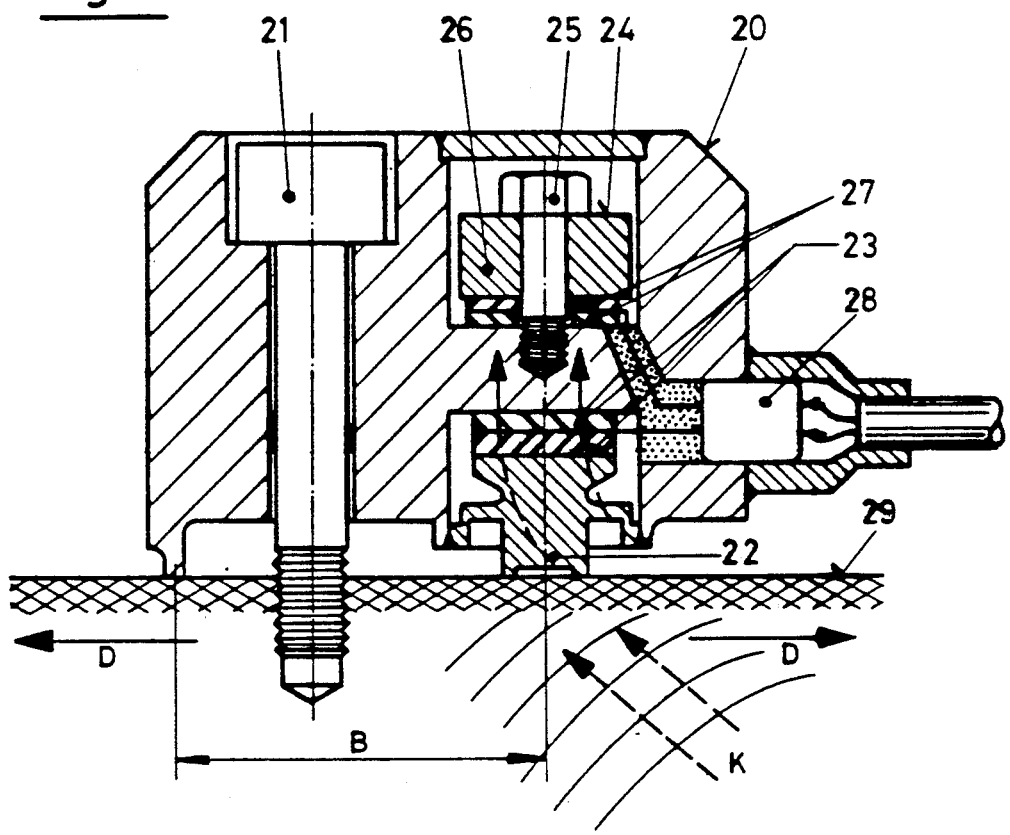
FIG. 4 is a cross-sectional view of a surface strain transducer with built in structure-borne noise sensor.
Figure 5:
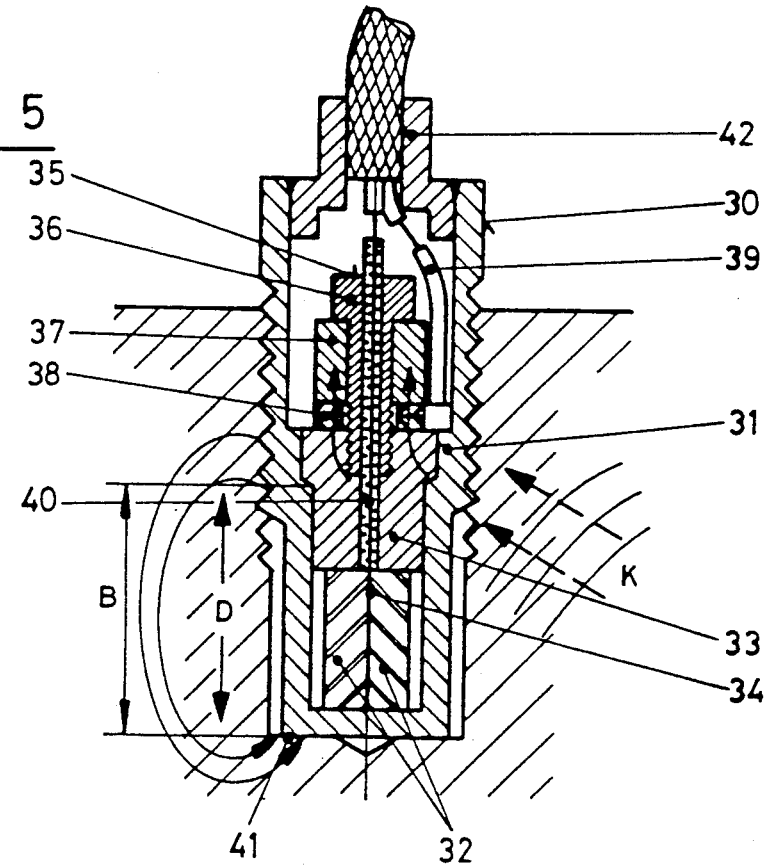
FIG. 5 is a cross-sectional view of a bore strain transducer with built in structure-borne noise sensor.

FIGS. 4 and 5 show strain sensors with built in single or multi-axis structure-borne noise sensor. Both transducer categories are based on piezoelectric metrology. The structure-borne noise sensor may include piezoelectric, piezorestrictive and capacitive sensors, among others. In both application groups, impedance transformer preamplifiers may be integrated in the sensors or the connector parts.

FIG. 1 shows a single or multi-component transducer for force and structure-borne noise according to the invention, consisting of a cover plate 2, a base plate 3 and, between these under preload, a crystal annulus set 4. Outer housing 10, tightly seals the transducer 1. According to requirements of the tool, the crystal annulus set 4 may detect one, two or three force components, i.e. Z forces or XY or XYZ forces. Quartz disks cut in different directions are used preferably for this, though piezo-ceramics may also be employed.

Accommodated in the bore of the crystal annulus set 4 is a structure-borne noise sensor 6 on the same mounting surface 19. The structure-borne noise sensor 6 consists of the crystal set 9, the mass 8 and the preloading screw 7 threaded into base plate 3.

The example in FIG. 1 shows a crystal arrangement for two force components and a single-component structure-borne noise sensor 6. The structure-borne noise sensor 6 is an accelerometer with a natural frequency above 50 kHz. Depending on the number of crystal arrangements, it can also be sensitive in several axes, like the force transducer. It may be advantageous to make the crystal set 9 sensitive in three directions XYZ, and connect all three signal electrodes together so that there is only one signal output.

It is advantageous to place in a connection socket 18 an impedance transformer/preamplifier 5, which is obtainable today in chip form and requires very little space. A connection cable 14 extends from the socket 18.

The structure-borne noise transducer 1 is fitted in a niche 11 under mechanical load, at a point where the various forces XYZ and the structure-borne noise signals K arrive and are transmitted further. For satisfactory transmission of structure-borne noise signals K, the contact between base plate 3 and mounting surface 19 must be as free as possible from air gaps.

FIG. 2 shows the same transducer 1, though with integrated preload nut 12. The cover plate 2 includes an extended threaded nipple projection 13. Accordingly the sensor 1 can be fitted force-conducting in any niche 11.

FIG. 3 shows a variant of FIG. 2. The cover plate 2 according to FIG. 1 includes an integral key plate 15, which is joined to an upper key plate 16 through a double screw 17. With this arrangement also, a force-conducting installation is possible in any niche 11.

FIG. 4 shows a surface strain transducer 20 with built in structure-borne noise sensor 24. The supporting head 22 transmits the strain to the shear crystal set 23, whose signal electrode is led straight into the impedance transformer/preamplifier 28. The supporting head 22 is pressed onto the measuring surface 29 by the screw 21. This provides ideal transfer conditions for impinging structure-borne noise waves K, so that they go straight to the structure-borne noise sensor 24. The structure-borne noise sensor 24 consists of the crystal annulus set 27, mass 26 and preload screw 25. Again, the crystal annulus set 27 may be sensitive in one or more axes. For the sake of simplicity, the signal electrodes are connected together for multiaxial sensitivity and led to the impedance transformer/preamplifier 28.

FIG. 5 shows a screw strain transducer 30 according to the invention. It is pressed against a press-on surface 41 with a screw body 31. Strains D resulting from force changes are transmitted onto a crystal set 32, whose signal is transmitted via the signal electrode 34 to a signal line 40. On a preload body 33 welded to the screw body 31 is the structure-borne noise sensor 35, whose mass 37 is braced over the crystal annulus set 38 by the preload screw 36 threaded into the preload body 33. The crystal annulus 38 can again be single- or multiaxial. In the multiaxial state, a connection into one single signal conductor 39 is also advantageous. In a connection socket 42, an impedance transformer/preamplifier can be accommodated as in the other Figures. The structure-borne noise waves K pass through the braced threaded part into the end support 33, on which the structure-borne noise sensor 35 is mounted. This in turn allows a good coupling to the wall parts surrounding the screw strain transducer.

The screw strain transducer 30 shown in FIG. 5 measures strain in the axial direction of the screw thread. Screw strain transducers are available commercially, however, which measure strains normal to the axial direction. With such devices, the installation of a structure-borne noise sensor also offers benefits. Its sensitivity may be axial or normal to the thread axis. Structure-borne noise sensors having multicomponent crystal sets can be employed as well.

As mentioned previously, fitting structure-borne noise sensors in force or strain sensors provides installation advantages. Moreover, the structure-borne noise sensors are brought as close as possible to the elements generating structure-borne noise. This enables the monitoring sensors to be located near to the process. In addition, the combined evaluation of the two signal types yields information which can simplify the complexity of structure-borne noise signal processing.

Universal monitoring systems of the future will have to process multiaxial forces, strains and structure-borne noise signals. The simpler the mounting of the transducers becomes, the more reliable the process monitoring can become. The invention thus enables the achievement of further progress towards computer-assisted process and plant monitoring.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed is:

1. A force/strain and structure-borne noise transducer comprising:
   a housing having a mounting surface through which force, strain and structure-borne noise are transmitted from a structure to which said mounting surface is mounted;
   one of a force or strain sensor in said housing for receiving force or strain respectively from said mounting surface; and
   a structure-borne noise sensor in said housing for receiving structure-borne noise from said mounting surface.

2. A force/strain and structure-borne noise transducer according to claim 1 wherein one sensor is an annular force sensor and said structure borne noise sensor is entirely in a central bore of said annulus.

3. Force/strain and structure-borne noise transducer according to claim 2 wherein said annular force sensor is responsive to forces along plural axes.

4. Force/strain and structure-borne noise transducer according to claim 2 wherein said annular force sensor includes quartz annuli.

5. Force/strain and structure-borne noise transducer according to claim 2 wherein said annular force sensor includes piezo-ceramic annuli.

6. Force/strain and structure-borne noise transducer according to claim 2 wherein said one sensor is a strain sensor of a surface strain transducer.

7. Force/strain and structure-borne noise transducer according to claim 2 wherein said one sensor is a strain sensor and said housing includes external threads to constitute a screw strain transducer.

8. Force/strain and structure-borne noise transducer according to claim 7 wherein said mounting surface is transverse to a main axis of the transducer and said strain sensor and said structure-borne noise sensor are sensitive along the main axis of the transducer.

9. Force/strain and structure-borne noise transducer according to claim 7 wherein said mounting surface is parallel to a main axis of the transducer said strain sensor and said structure-borne noise sensor are sensitive along an axis transverse to the main axis of the transducer.

10. Force/strain and structure-borne noise transducer according to claim 2 wherein said housing includes an integral threaded area and a thread nut for preloading said transducer between two surfaces of a machine to be monitored.

11. Force/strain and structure-borne noise transducer according to claim 2 wherein said housing includes an integral key plate, a separate mating key plate and a bracing screw between said key plates.

12. Force/strain and structure-borne noise transducer combination according to claim 1, wherein said structure-borne noise sensor has multi-axial sensitivity.

13. Force/strain and structure-borne noise transducer according to claim 1, wherein said structure-borne noise sensor is piezoelectric 14. Force/strain and structure-borne noise transducer according to claim 1, wherein said structure-borne noise sensor is piezoresistive.

15. Force/strain and structure-borne noise transducer according to claim 1 wherein said structure-borne noise sensor is capacitive.

16. Force/strain and structure-borne noise transducer according to claim 2, including impedance transformer/preamplifiers in said housing for providing separate signals from said sensors.

* * * * *